(12) United States Patent
Yoo et al.

(10) Patent No.: US 10,022,415 B2
(45) Date of Patent: Jul. 17, 2018

(54) **EXTERNAL COMPOSITION FOR SKIN CONTAINING AN ENZYME-TREATED SAPONIN FRACTION DERIVED FROM THE ROOT OF *CAMELLIA SINENSIS***

(71) Applicant: AMOREPACIFIC CORPORATION, Seoul (KR)

(72) Inventors: Se Jin Yoo, Yongin-si (KR); Sun A Cho, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 447 days.

(21) Appl. No.: 14/931,182

(22) Filed: Nov. 3, 2015

(65) Prior Publication Data

US 2016/0120929 A1    May 5, 2016

(30) Foreign Application Priority Data

Nov. 3, 2014  (KR) ........................ 10-2014-0150909

(51) Int. Cl.
| | | |
|---|---|---|
| *A61K 36/00* | (2006.01) | |
| *A61K 36/82* | (2006.01) | |
| *A61Q 19/08* | (2006.01) | |
| *A61Q 19/00* | (2006.01) | |
| *A61K 8/97* | (2017.01) | |
| *A61Q 19/02* | (2006.01) | |

(52) U.S. Cl.
    CPC .............. *A61K 36/82* (2013.01); *A61K 8/97* (2013.01); *A61Q 19/007* (2013.01); *A61Q 19/02* (2013.01); *A61Q 19/08* (2013.01); *A61K 2800/85* (2013.01)

(58) Field of Classification Search
    CPC ...................................................... A61K 36/00
    USPC ....................................................... 424/725
    See application file for complete search history.

(56) References Cited

U.S. PATENT DOCUMENTS 6,099,844 A * 8/2000 Rohde, Jr. ........ C12Y 302/01004
                                                        424/727

\* cited by examiner

*Primary Examiner* — Michael V Meller
(74) *Attorney, Agent, or Firm* — Nixon & Vanderhye P.C.

(57) ABSTRACT

The present invention relates to a composition comprising the saponin fraction derived from the root of *camellia sinensis*, and more specifically, a composition which, by using the saponin fraction isolated after treating the extract of the root of *camellia sinensis* with an enzyme, can reduce the cellular toxicity over the conventional saponin fraction derived from the root of *camellia sinensis* to enhance stability to the skin, and can comprise the saponin fraction obtained by such method in much higher amounts to provide the more superior skin condition improvement effect.

1 Claim, 1 Drawing Sheet

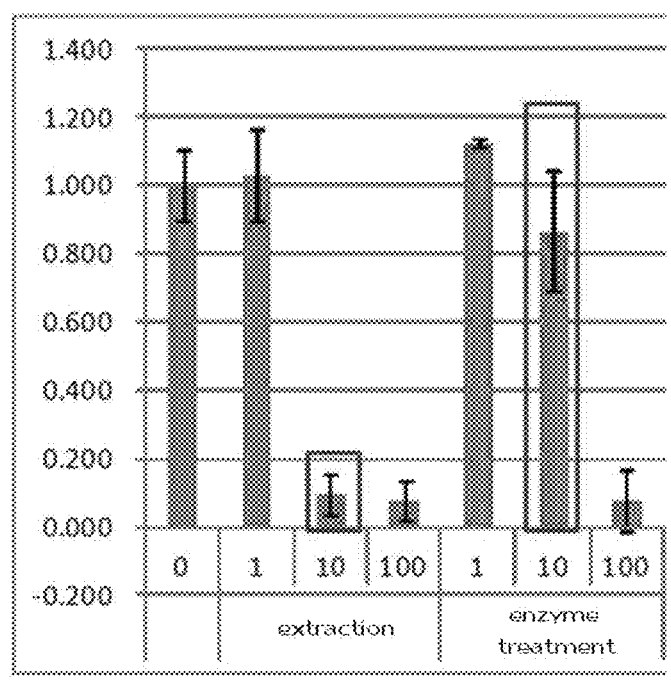

EXTERNAL COMPOSITION FOR SKIN CONTAINING AN ENZYME-TREATED SAPONIN FRACTION DERIVED FROM THE ROOT OF *CAMELLIA SINENSIS*

This application claims priority to KR Patent Application No. 10-2014-0150909 filed 3 Nov. 2014, the entire contents of which is hereby incorporated by reference.

TECHNICAL FIELD

The present invention relates to a composition containing saponin fraction from the roots of *camellia sinensis*, and more specifically relates to the composition which uses saponin fraction which is obtained by treating the extracts of roots of *Camellia sinensis* with an enzyme and then isolating it to enhance the safety to a skin by lowering the cell toxicity when comparing the existing saponin fraction extracted from *Camellia sinensis*, and which can comprise a high degree of the saponin fraction, as obtained such manner, to provide the more excellent skin condition-improvement effects.

BACKGROUND ART

A skin of a human is a primary barrier of a human body and has a function protecting the organ in a body from a stimulus of an outer circumstance such as a change of a temperature and moisture, ultraviolet ray, pollutant, and the like, and undergoes a change by various inner and outer factors. That is, internally, a secretion of various hormones regulating metabolisms is reduced, a function and activity of immune cells are lowered, and thus, a biosynthesis of immune proteins necessary for an body and proteins constituting the body are decreased, and externally, a content of ultraviolet ray reaching the surface of an earth is increased due to a destruction of an ozone layer and free radicals, active harmful oxygen and the like are increased as an environment pollution is deepening, and thus various changes are raised such as that the thickness of a skin is reduced, a wrinkle is increased, an elasticity of the skin is reduced, as well as, a bloom of the skin is dull, a trouble of the skin is often occurred, chloasmas, freckles and age spots are increased, the bloom of the skin becomes worse, a skin tone becomes dark, and the like.

In order to prevent changes of the skin condition due to the internal or external factors and to maintain the healthy skin condition, there has been efforts to improve the skin condition by adding the physiological active materials obtained from the already known various animals, plants, microorganisms and the like to cosmetics and using it.

Meanwhile, green tea uses leaves of *Camellia sinensis*, and is consumed as a medical beverage and healthy drinks, and the medical effects of the green tea is due to flavonoid-based ingredients. Several of triterpenoid saponin extracted from leaves of *Camellia sinensis* is reported as bitter principle and triterpenoid saponin can be also extracted from other parts of *Camellia sinensis*, i.e., seeds, flower buds, roots, etc.

In particular, triterpenoid saponin derived from roots of *Camellia sinensis* provides an excellent skin improvement effect such as anti-aging, skin whitening, skin moisturizing and the like, but since it has a toxicity itself, there are problems in the light of the skin safety in the case of that it is used in large amounts, and thus, there is a need to lower the toxicity of the saponin derived from roots of *Camellia sinensis*.

PRIOR ART LITERATURE

Patent Literature (Patent Literature 1) Korean Patent Application No. 2011-0099527.

DISCLOSURE

Technical Problem

Therefore, inventors of the preset invention tried to provide saponin having a low toxicity, as derived from roots of *Camellia sinensis* to enhance the skin safety, and founded that when extracts of roots of *Camellia sinensis* are treated with an enzyme, the toxicity of saponin fraction can be greatly lowered, and then, completed the present invention.

Accordingly, the object of the present invention is to provide the method for reducing the toxicity of the saponin fraction derived from roots of *Camellia sinensis*, and the composition which can comprise large amounts of the saponin fraction having a low toxicity, as derived from roots of *Camellia sinensis* than the existing composition.

Means for Resolving the Problem

In order to achieve said objects, the present invention provides the composition for external use of the skin, which comprises the enzyme-treated saponin fraction derived from the extract of the roots of *Camellia sinensis* as an active ingredient.

In addition, the present invention provides the method for lowering the toxicity of the saponin fraction derived from the root-extracts of *Camellia sinensis*.

Advantageous Effects

A method according to the present invention can effectively reduce the toxicity of the saponin fraction derived from the root-extracts of *Camellia sinensis*, since the saponin fraction having the low toxicity made by such method has the lower cellular toxicity and the improved skin safety, it can be comprised in the composition in greater amounts more than the conventional saponin fraction derived from the extracts of roots of *Camellia sinensis*, and thus, it can provide the skin improvement effect more effectively and exhibits more excellent skin wrinkle improvement effect, skin whitening effect, the skin moisturizing and atopic skin improvement effect, acne and the skin trouble improvement effect, and skin bloom improvement effect.

DESCRIPTION OF DRAWINGS

FIG. 1 exhibits the results comparing the cellular toxicity of the enzyme-treated saponin fraction derived from *Camellia sinensis* roots with no enzyme-treated saponin fraction derived from *Camellia sinensis* roots.

BEST MODE FOR INVENTION

A composition for the external application to the skin according to the present invention comprises the extracts derived from the enzyme-treated *Camellia sinensis* roots, specifically the saponin fraction, more specifically triterpenoid saponin, as an active ingredient.

The saponin fraction used in the present invention comprises 10 kinds of triterpenoid saponin derived from roots of *Camellia sinensis*, more specifically tripenoid saponin isolated from alcohol extract such as methanol, ethanol and the like of roots of *Camellia sinensis*, and the triterpenoid saponins are referred to as 'saponins R1-R10 derived from roots of *Camellia sinensis*' in the present invention. Such saponins R1-R10 derived from roots of *Camellia sinensis* have structures represented by chemical formulae of 1 to 10 as follows.

[Chemical formula 1]

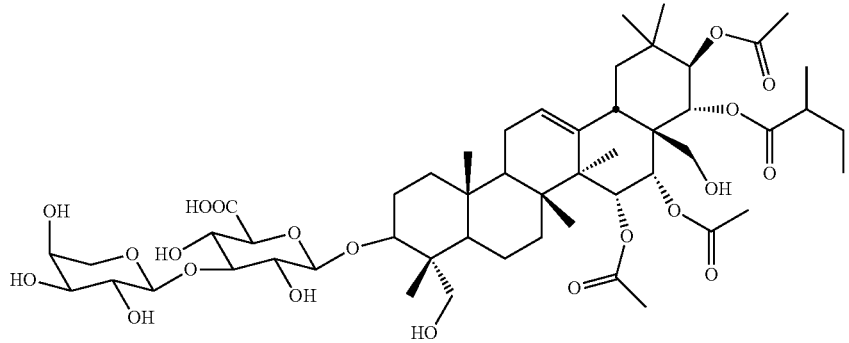

Saponin R1 derived from roots of Camellia sinensis

[Chemical formula 2]

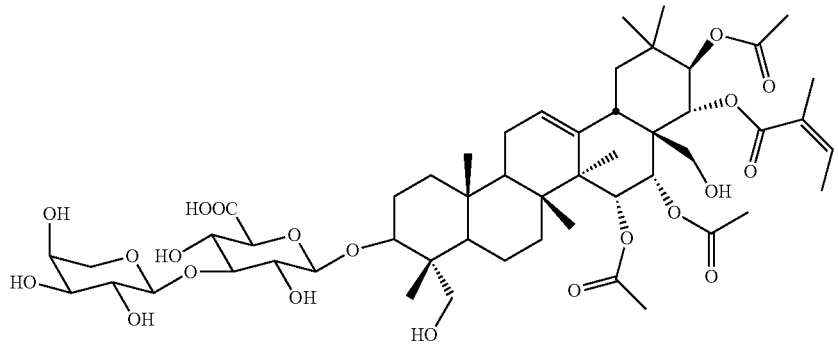

Saponin R2 derived from roots of Camellia sinensis

[Chemical formula 3]

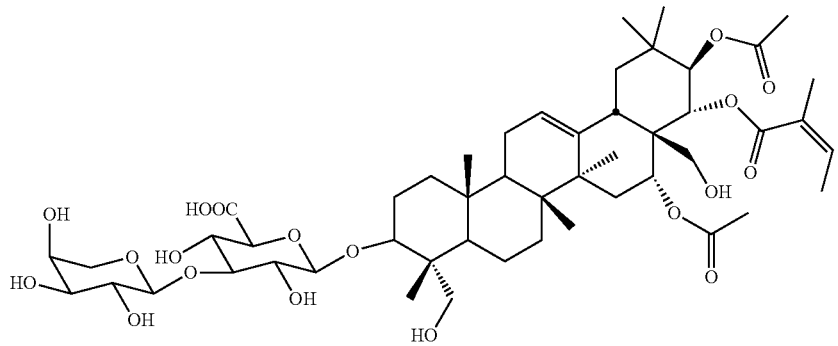

Saponin R3 derived from roots of Camellia sinensis

-continued
[Chemical formula 4]
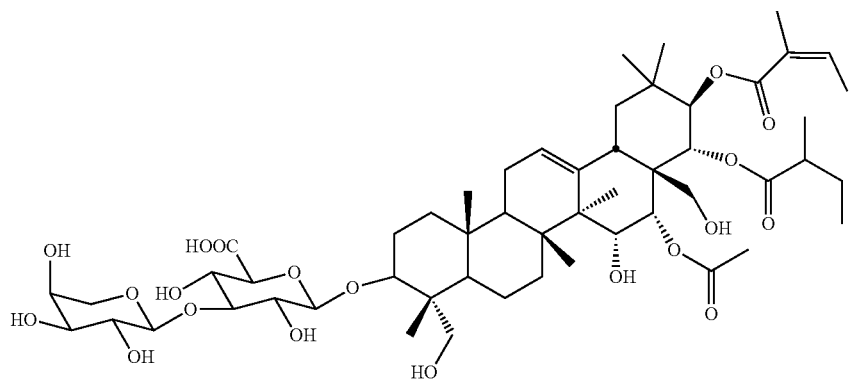
Saponin R4 derived from roots of Camellia sinensis
[Chemical formula 5]
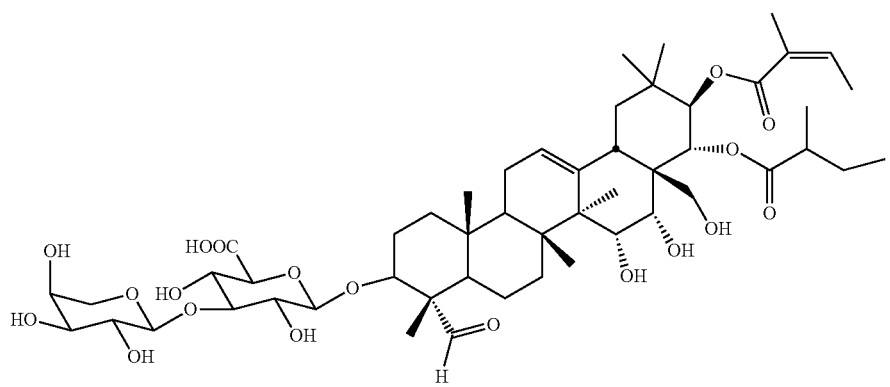
Saponin R5 derived from roots of Camellia sinensis
[Chemical formula 6]
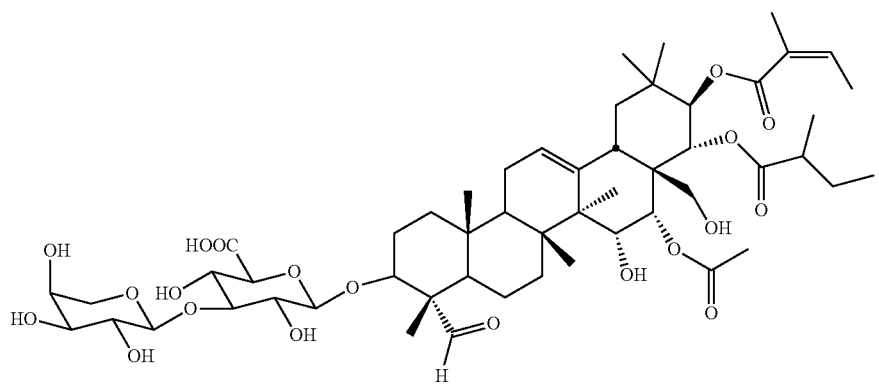
Saponin R6 derived from roots of Camellia sinensis -continued
[Chemical formula 7]
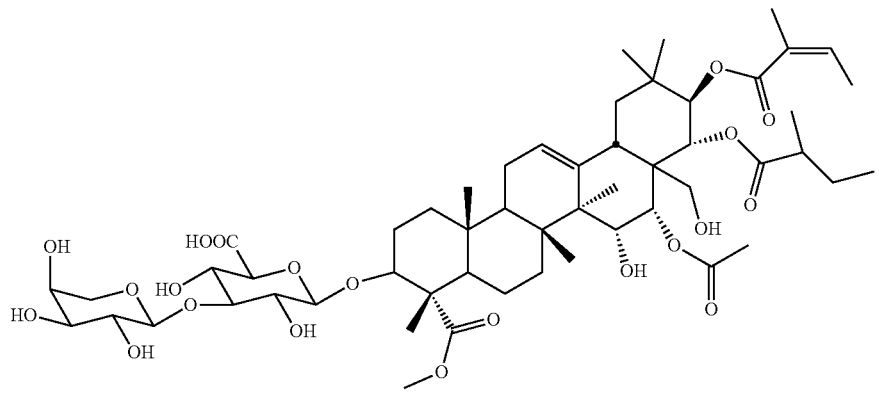
Saponin R7 derived from roots of Camellia sinensis
[Chemical formula 8]
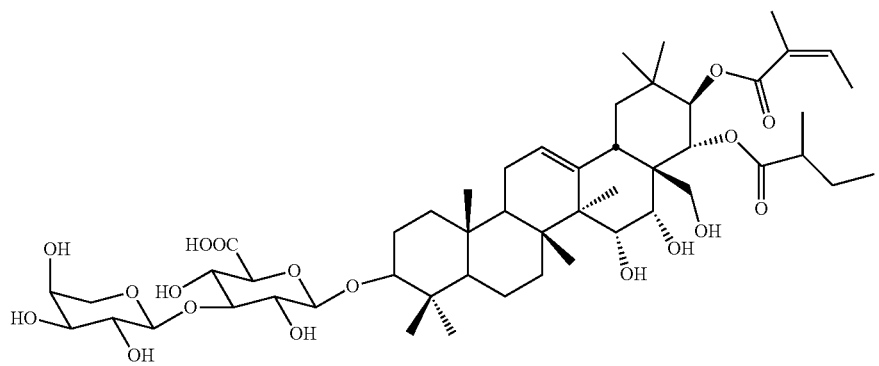
Saponin R8 derived from roots of Camellia sinensis
[Chemical formula 9]
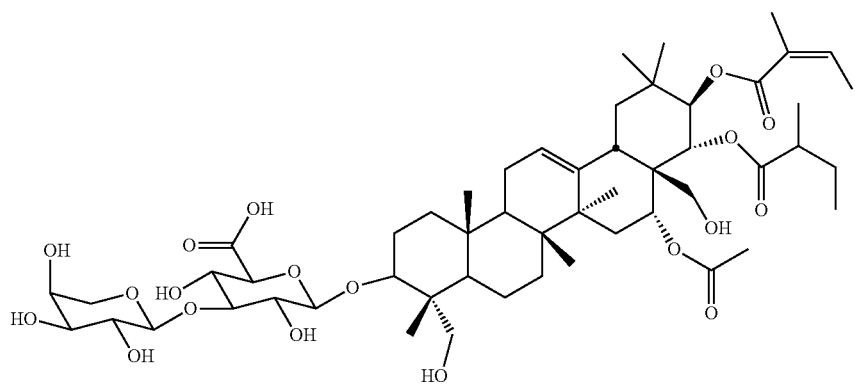
Saponin R9 derived from roots of Camellia sinensis

[Chemical formula 10]

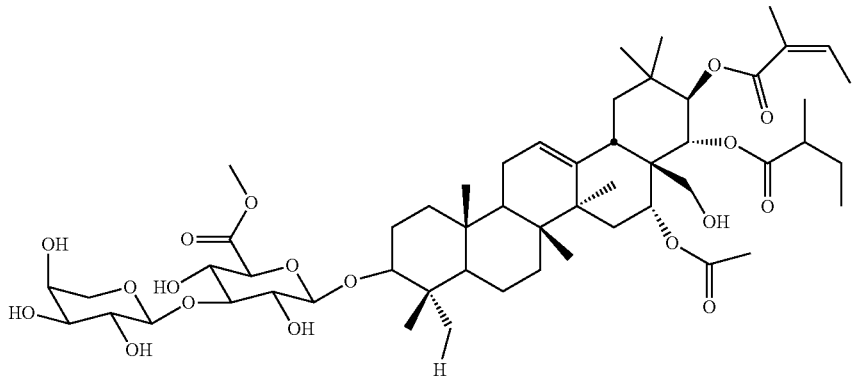

Saponin R10 derived from roots of Camellia sinensis

Since the saponin derived from roots of *Camellia sinensis* has a toxicity itself, there is a problem causing a skin stimulation due to the cellular toxicity when it is used in large amounts.

In order to solve such problem, the present invention uses saponin fraction in which the extract derived from roots of *Camellia sinensis* is treated with an enzyme. Specifically, the present invention can use one or more kinds of enzymes selected from the group consisting of glucosidase, xylosidase, xylanase, galactosidase, naringinase, pectinase, cellulase, hemicellulase and arabinase, preferably one or more kinds of enzymes selected from the group consisting of pectinase, cellulase, hemicellulase and arabinase in treating the extract derived from roots of *Camellia sinensis*. In addition, it is preferable that the treatment using said enzymes is performed at pH 3.5~5.0, preferably pH 4.2~4.7, at the temperature of 25~60° C., preferably at the temperature of 30~50° C. for 1~48 hours. When saponin fractions derived from roots of *Camellia sinensis* are isolated from the enzyme-treated extracts by using the known isolation method, saponin fractons having the lower toxicity can be obtained.

It is preferable that the composition of the present invention comprises said saponin fraction in an amount of 0.1~50% by weight (wt %) to the total weight of the composition. This is due to that when the content of the effective ingredient is less than 0.1 wt %, the efficacy and effects are weak, and when it is greater than 50 wt %, there are problems on the skin safety or formulation.

The composition of the present invention comprises the enzyme-treated saponin fraction derived from the extract of roots of *Camellia sinensis* as an active ingredient, and thus can effectively provide various skin condition-improvement effects.

The composition of the present invention can be used as the anti-aging composition for external application to skin, and it have the excellent effects for improving the elasticity and wrinkle of the skin.

The composition of the present invention can be used as the moisturizing composition for external application to the skin, and it can strengthen the function of the skin barrier and can derive a differentiation of the keratinocytes of the skin. Therefore, it can be usefully used as the composition for the external application to the skin, for preventing or improving xeroderma, atopic dermatitis, contact dermatitis, psoriasis, etc. caused by a defectiveness of the epidermis differentiation.

The composition of the present invention can be used as an acne-improving composition for external application to the skin, and it is good at antibiotic effect, in particular, the antibiotic effect for causative organisms of acne, and also provides an inflammative effect.

The composition of the present invention can be used as the bloom- and skin tone-improving composition for the external application to the skin, and when applying it to the skin, it smoothly provides nutrients to the skin by facilitating the circulation of the blood and has excellent effects for improving bloom and skin tone by inhibiting the aging of the skin.

The composition of the present invention can be used as a pore tightening, sebum controlling and skin trouble improving composition for external application to the skin, and when it is applied to the skin, it can inhibit sebum excessively secreted, facilitate the removal of the active oxygen and the synthesis of collagen to reduce the pore and has the excellent effect for inhibiting the skin troubles due to the expression reduction of inflamatory factors. Also, it can protect a generation of the skin stimulation due to the excellent anti-oxidizing force.

The composition of the present invention can be used as the composition for improving the atopic skin, and it can provide the excellent antipruritic effects by inhibiting an activity of Proteinase-Activated Receptor-2 (PAR-2) causing itching, as well as, it can provide the anti-inflammation effect through the reduction of the secretion for the Interleukin-8 (IL-8). Therefore, the saponin of the present invention can be used as the active ingredient of the composition for external application to the skin, for stabilizing the sensitive, stimulating or atopic skin and scalp and for improving or alleviating itching, heat sensation and inflammation.

The composition of the present invention can be used as a skin-whitening composition, and it can provide the excellent skin-whitening effect by hindering tyrosinase activity and by inhibiting a generation of melanin.

The composition of the present invention can be formulated to comprise the cosmetically or dermatologically acceptable media or bases. It can be provided as all the formulations for the topical application, for example, in the form of solution, gel, solid, pasty anhydrous product, emulsion obtained by dispersing an oil phase in water phase, suspension, microemulsion, microcapsule, microgranule or ionic form (liposome) and vesicle dispersant of non-ionic form, or in the form of cream, skin, lotion, powder, ointment, spray or conceal stick. In addition, it can be used as aerosol composition in a foam form or as the aerosol composition comprising additional amounts of the compressed propellant. These compositions can be prepared by the conventional method in the relevant art.

In addition, the composition of the present invention can comprise an adjuvant generally used in the cosmetical or dermatological fields, such as a fat material, organic solvent, solubilizer, concentrating agent, gelling agent, softening agent, anti-oxidant, suspending agent, stabilizing agent, foaming agent, flavoring agent, surfactant, water, ionic or non-ionic emulsifying agent, filler, sequestering agent, chelating agent, preservative, vitamin, blocking agent, moisturizing agent, essential oil, dye, pigment, hydrophillic or hydrophobic activator, lipid droplet or the optional other components conventionally used in the cosmetics. The adjuvant is introduced in the amounts generally used in the cosmetical or dermatological fields.

In addition, the composition of the present invention can comprise the material facilitating the absorption of the skin so as to improve the skin improvement effect.

Hereinafter, the constitution and the effects of the present invention will be illustrated in detail in reference to Examples and Formulation Examples. But, the Examples and Formulation Examples is given for only an illustrative purpose to help the understanding of the present invention and the scope and range of the present invention are not intended to be limited to the below Examples.

Example 1

A Preparation of Saponin Fraction of the Enzyme-Treated Extract Derived from Root of *Camellia sinensis*

Roots of *Camellia sinensis* tree was obtained from the *Camellia sinensis* of *Yabukita* species aged 30 years (collected from Hannam-ri, Namwon-eup, Seogwipo-si, Jeju-do, Korea). 10 kg of root of the *Camellia sinensis* tree was minced into small pieces, soaked into 8 L of 80% aqueous MeOH and left at the room temperature for two days, and such extraction step was repeated twice. The extract was filtered with 0.5 μm filter and clear red-brown liquid was obtained. The filtrate obtained above was treated with Multifect Pectinase FE (Genencor Int., Rochester, N.Y.; the high concentrated pectinase combination comprising pectinase, cellulase, hemicellulase and arabinase) (0.1%), at pH 4.5, at the temperature of 60° C. for 1 day.

100 g of the material treated above was separated by a chromatography using C18 silica gel flash column with 0-100% of MeOH in $H_2O$ (each of 4 L) increased by 10%, as an eluent and then eleven fractions (A to K) were obtained. The active fraction G (60% MeOH was used; 4 g) and H (70% MeOH was used; 10 g) among them were combined, the chromatography using the silica gel flash column was repeatedly performed by using 0-100% MeOH increased by 10% as an eluent to give eight fractions (GH1 to GH8).

Saponin fraction GH5 (1.02 g) in the fractions was obtained and then used in the below Experimental Examples.

Comparative Example 1

The preparation of saponin fraction of the no enzyme-treated extracts derived from the root of *Camellia sinensis*.

Saponin fraction samples were obtained by using the same procedure of the above Example 1, except that the extract of the root of the *Camellia sinensis* tree was not treated with the enzyme.

Experimental Example 1

Estimation for the Cellular Toxicity

A degree of the cell toxicity of saponin fractions derived from root of the *Camellia sinensis*, as obtained in the above Example 1 and Comparative Example 1, was identified by using CCK-8 kit (Dojindo).

The result is represented in FIG. 1.

As shown in FIG. 1, when 1 ppm of the no enzyme-treated saponin fraction derived from the root of *Camellia sinensis* was treated, there is no cellular toxicity, but when 10 ppm of it was treated, there is the cellular toxicity and thus it is not proper for the use, but it can be identified that the enzyme-treated saponin fraction derived from the root of *Camellia sinensis* did not strongly exhibit the cellular toxicity, even when 10 ppm was treated.

Experimental Example 2

Determination of the Efficacy for the Inhibition of Elastase Activity

An ability hindering elastase activity of the enzyme-treated saponin fraction derived from the root of *Camellia sinensis* was determined in comparison with EGCG. The elastase and substrate as used were commercially purchased from Sigma Aldrich in U.S.A (Cat. No. E0127), and the saponin fraction was used as the enzyme-treated saponin fraction derived from the root of *Camellia sinensis* roots as obtained from Example 1.

The action for hindering elastase activity was examined by the below Experimental method.

50 μL of Test material as represented in the below Table 1 and 20 μg/mL elastase·50 μL of solution of type III were mixed with that prepared with 10 mg/L Tris-HCl buffer (pH 8.0) in 96-well plate. 250 μM of EGCG was used as a positive control, and non-treated group as a negative control used the distilled water. Then, 100 μL of 0.4514 mg/mL N-SUCCINYL-ALA-ALA-p-NITROANILIDE prepared with the above buffer was added, and reacted at the temperature of 25° C. for 15 minutes. After completing the reaction, the absorption at the wavelength of 415 nm was determined. The blank experiment was performed by using the same procedure and then compensated.

The calculation method for the action for hindering the elastase activity is the same as a mathematical formula as below, and the result is represented in the below Table 1.

Hindering rate of elastase activity (%)={1−(C−D)/(A−B)}×100     [Mathematical formula 1]

A: No addition of the experimental sample, Absorbance at the wavelength of 415 nm with the addition of enzyme B: No addition of the experimental sample, Absorbance at the wavelength of 415 nm without the addition of enzyme C: Addition of the experimental sample, Absorbance at the wavelength of 415 nm with the addition of enzyme D: Addition of the experimental sample, Absorbance at the wavelength of 415 nm without the addition of enzyme

TABLE 1

| Experimental material | Degree of the inhibiton (%) |
|---|---|
| Non-treated group | 0 |
| EGCG | 65 |
| Enzyme-treated saponin fraction derived from the root of camellia sinensis | 69 |

As shown in the above Table 1, since it is exhibited that the degree for hindering the elastase activity of the enzyme-treated saponin fraction derived from the root of *camellia sinensis* was excellent when comparing with EGCG known as the elastase activity inhibitor, it can be identified that the effect for inhibiting elastase activity of the enzyme-treated saponin fraction of the present invention was excellent.

Experimental Example 3

Ability for Hindering Collagenase (MMP-1)

The ability for hindering collagenase generation of the enzyme-treated saponin fraction derived from the root of *Camellia sinensis* of the present invention was determined in comparison with retinoic acid.

Fibroblast of a human was placed in 96-well plate (96-well microtiter plate) with Dulbecco's Modified Eagle's Media (DMEM) containing 2.5% fetal bovine serum to be 5,000 cells/well, and was cultured at 5% $CO_2$, at the temperature of 37° C. of incubator to grow to about 70~80% confluency. The saponin fraction derived from the root of *Camellia sinensis* of the above Example 1 was treated for 24 hours in a concentration of 30 μg/ml, and then the cell culture was collected.

The degree of the collagenase generation for the cell culture collected by using the commercially available collagenase determination Apparatus (AmershamPharmacia Corporation in U.S.A., Catalog #: RPN 2610) was determined. At first, the collected cell culture was placed in 96-well plate evenly covered with the first collagenase antibody and antigen-antibody reaction was performed in thermostat container for three hours. After 3 hours, the secondary collagen antibody bound with chromophore was placed in 96-well plate and reacted for 15 minutes. After 15 minutes, chromogen-inducing material, 3,3',5,5'-tetramethylbenzidine (sigma) was placed to cause the chromogen at the room temperature for 15 minutes, stopped the chromogenic reaction by adding 1M sulfuric acid again, and then the color of the reaction was appeared with yellow and the degree of the yellow color was differently appeared according to the degree of the reaction proceeding.

The absorbance of 96-well plate representing yellow color was determined by using Absorptiometer at 405 nm, the degree of collagenase synthesis was calculated by the below Mathematical formula 2, and the result was shown in Table 2 as below. In this case, the absorbance for the reaction of the cell culture collected from the group without treating with the composition was used as the control.

$$\text{Degree of the collagenase expression (\%)} = \frac{\text{Absorbance of the material-treated cell group}}{\text{Absorbance of the control}} \times 100$$

[Mathematical formula 2]

TABLE 2

| Experimental materials | Degree of the expression (%) |
|---|---|
| Non-treated group | 100 |
| Retinoic acid | 75 |
| Enzyme-treated saponin fraction derived from the root of Camellia sinensis | 78 |

As shown in the above Table 2, it can be seen that the degree of the collagen expression of the enzyme-treated saponin fraction derived from the root of *Camellia sinensis* was remarkably excellent even when comparing retinoic acid known as the collagenase expression inhibitor.

Through such the result, it can be identified that the enzyme-treated saponin fraction derived from the root of *Camellia sinensis* has the effect hindering the matrix metalloproteinase (MMP-1).

Formulation Example 1 and Comparative Formulation Example 1

A nourishing cream was prepared by the conventional method according to the composition of Table 3 as below (Unit: wt %).

TABLE 3

| Combination ingredients | Formulation Example 1 | Comparative Formulation Example 1 |
|---|---|---|
| Purified water | To 100 | To 100 |
| Enzyme-treated saponin fraction derived from the root of Camellia sinensis | 0.1 | — |
| Hydrogenated vegetable oil | 1.50 | 1.50 |
| Stearic acid | 0.60 | 0.60 |
| Glycerol stearate | 1.00 | 1.00 |
| Stearyl alcohol | 2.00 | 2.00 |
| Polyglyceryl-10 pentastearate & Behenyl alcohol & Sodium stearoyl lactilate | 1.00 | 1.00 |
| Arachidyl behenyl alcohol & Arachidyl glucoside | 1.00 | 1.00 |
| Cetylaryl acohol & Cetearyl glucoside | 2.00 | 2.00 |
| PEG-100 stearate & Glycerololeate & Propylene glycol | 1.50 | 1.50 |
| Caprylic/Capric triglyceride | 11.00 | 11.00 |
| Cyclomethicone | 6.00 | 6.00 |
| Preservative, perfume | q.s. | q.s. |
| Triethanol amine | 0.1 | 0.1 |

Experimental Example 4

Identification of the Efficacy for the Improvement of the Elasticity of the Skin In order to identify the effect for the improvement of the skin elasticity, the estimation was performed with the above Formulation Example 1 and the Comparative Formulation Example 1, as follows.

Twenty of the healthy women aged 30~40 were divided into two groups with each of ten women for two groups of the Formulation Example 1 and the Comparative Formulation Example 1, respectively and after applying the nourishing cream on the left of face once a day for 12 weeks, the skin elasticity was determined by using Skin elasticity tester (Cutometer SEM 575, C+K Electronic Co., Germany). The result was represented in Table 4 as below. The result values of Table 4 were described as ΔR8(R8 (left)-R8 (right)) value of Cutometer SEM 575, and R8 value represents the property of the skin viscoelasticity.

| Experimental products | Effect of the skin elasticity |
|---|---|
| Formulation Example 1 | 0.21 |
| Comparative Formulation Example 1 | 0.10 |

As shown on Table 4 as above, the Formulation Example 1 comprising the enzyme-treated saponin fraction derived from the root of *Camellia sinensis* of the present invention increases the skin elasticity greater than the group applied with the Comparative Formulation Example 1.

Therefore, it can be identified that the composition comprising the enzyme-treated saponin fraction derived from the root of *Camellia sinensis* is very effective in improving the skin elasticity.

Experimental Example 5

Identification of the Skin Wrinkle-Improving Effect

In order to identify the wrinkle-improving effect in the human by the composition of the present invention, the above Formulation Example 1 and the Comparative Formulation Example 1 were used.

In order to identify the skin wrinkle-improving effect for the above Formulation Example 1 and the Comparative Formulation Example 1, the estimation was performed as follows. Twenty of the healthy women aged 40 were divided into two groups with each of ten women for two groups of the Formulation Example 1 and the Comparative Formulation Example 1, respectively and after applying the nourishing cream on the face once a day for 12 weeks, a replica was copied by using silicone, and then the condition of the wrinkle was determined by the visiometer, SV600 (Courage+Khazaka electronic GmbH, Germany) and an image analysis was performed. Its result is represented in Table 5 as below. The value of the below Table 5 is an average of those parameter value before the application subtracted from each parameter after 12 weeks of the application.

TABLE 5

| | A clinical result after 8 weeks of use | | | | |
|---|---|---|---|---|---|
| | R1 | R2 | R3 | R4 | R5 |
| Formulation Example 1 | 0.15 | 0.14 | 0.14 | 0.02 | 0.02 |
| Comparative Formulation Example 1 | 0.27 | 0.26 | 0.21 | 0.03 | 0.03 |

R1: value of difference between the highest value and the lowest value of a Contour of the wrinkle
R2: the average of R1 values after optionally dividing the Contour of the wrinkle into five (5) columns
R3: the highest value among R1 values of the Contour of the wrinkle divided into 5 columns
R4: the average value substrated each of top value and valley value from the baseline of the Contour of the wrinkle
R5: the value of difference of the value substrated each of the wrinkle line from the baseline of the Contour of the wrinkle As shown in Table 5 as above, it can be seen that the external applying composition of the Formulation Example 1 was very excellent in the skin wrinkle-improving effect.

Experimental Example 6

The Bloom-Improving Effect

In order to estimate the effect for facilitating the blood circulation of the skin of the cosmetical composition of the present invention, the degree of the blood circulation on the skin was determined with Laser Doppler Perfusion Imager (LDPI). LDPI has been widely known as an instrument determining the blood circulation on the skin and is the instrument being currently used, and is a very sensitive instrument which can determine the speed and amount of the blood on the capillary of the skin as well as even the flow on an arteriole and venula.

After washing the face with a soap in a constant temperature and humidity room, and adapting it for 30 minutes, the initial value was determined with LDPI. At first, the amount of the initial blood flow on the lower part of forehead of twenty women who has the cool hands and feet was determined with LDPI. And then, twenty women were divided into two group with each one having ten women and after allowing subjects to use two groups of the above Formulation Example 1 and the Comparative Formulation Example 1 for 1 week, respectively, the result comparing the amount of the blood flowing as determined and the above initial determining value with each other (the change of the amount of the skin blood flow) is represented in Table 6 as below.

TABLE 6

| LDPI result before and after using the cosmetic-the amount of skin blood flow | |
|---|---|
| Experimental materials | the variance rate of the skin-blood flow after 1 week of the use (%) |
| Formulation Example 1 | 15 |
| Comparative Formulation Example 1 | 5 |

From the result of the above Table 6, the cosmetic composition of the present invention greatly increased the amount of the skin blood flow more than the Comparative Formulation Example 1 without the enzyme-treated saponin fraction derived from the root of *camellia sinensis*, and it could be identified that the bloom was improved through the promotion of the blood circulation. It means that the cosmetic composition comprising the enzyme-treated saponin fraction derived from the root of *camellia sinensis* of the present invention contributes in effectively delivering nutrients of the skin, and inhibiting and delaying the skin aging.

Experimental Example 7

The Effect of the Skin Tone Improvement

In order to find the skin tone-improvement effect of the above Formulation Example 1 and the Comparative Formulation Example 1, twenty subjects were divided into two groups with one having 10 subjects and after using two groups of the above Formulation Example 1 and the Comparative Formulation Example 1, respectively (one per night/day of applying, for total 1 week), the degree of the improvement of the skin tone was estimated by using Facial Stage DM-3 (Moritex, Japan). The skin tone-improvement rate was determined with the determination values of the brightness and color determination values and the change value of the brightness and color of the skin, and the result is represented in the below Table 7.

TABLE 7

| Experimental materials | Improvement rate of the skin tone (%) | |
|---|---|---|
| | brightness (average ± standard deviation) | color (average ± standard deviation) |
| Formulation Example 1 | 10 ± 1.34 | 12 ± 2.15 |
| Comparative Formulation Example 1 | 5 ± 2.34 | 5 ± 2.05 |

From the result of the above Table 7, it was identified that the Comparative Formulation Example 1 without the enzyme-treated saponin fraction derived from the root of *camellia sinensis* of the present invention does not exhibit the significant skin tone-improvement efficacy, but the Formulation Example 1 comprising the saponin fraction derived from the root of *camellia sinensis* as the active ingredient improves the skin tone after the use of it much more than that before the use.

Experimental Example 8

The Pore-Tightening Effect

<The Pore-Tightening Effect Through the Promotion of the Collagen Biosynthesis>

In order to investigate the promoting effect of the collagen biosynthesis, the enzyme-treated saponin fraction derived from the root of *camellia sinensis* of the present invention was determined in comparison with TGF-β. At first, fibroblast was seeded as $10^5$ cells per a well in 24-well plate and cultured until growing to about 90% confluency. After incubating it with non-serum DMEM medium for 24 hours, it was treated with 10 ng/ml of the saponin fraction derived from the root of *camellia sinensis* of the above Example 1 and TGF-β dissolved in the non-serum medium, respectively and incubated in $CO_2$ incubator for 24 hours. The supernatant of them was taken and it was examined as to whether procollagen was increased or not by using procollagen type I ELISA kit. The result is represented in Table 8, and the ability for synthesizing the collagen was compared by considering that the non-treated group was 100.

TABLE 8

| Experimental materials | Ability for synthesizing collagen (%) |
|---|---|
| Non-treated group | 100 |
| TGF-β | 183.5 |
| Enzyme-treated saponin fraction derived from *camellia sinensis* | 135.1 |

From the result of the above Table 8, it could be identified that the enzyme-treated saponin fraction derived from *camellia sinensis* of the present invention exhibits the high level of the excellent ability for synthesizing collagen. Therefore, it could be identified that the enzyme-treated saponin fraction derived from the root of *camellia sinensis* of the present invention can increase the amounts of collagen generation around the pore of the skin and thus tighten the widen pore.

The Effect for Tightening the Pore of the Skin

In order to investigate the pore-tightening effect for the Formulation Example 1 and the Comparative Formulation Example 1, the following was estimated. Subjects, twenty of men and women who have widen pore sizes were selected, and divided into two groups, each one having 10 and then allowed them to apply the nourishing cream of the Formulation Example 1 and the Comparative Formulation Example 1 every day for 4 weeks for each group. A judgment for the pore-tightening effect was made by the naked-eye estimation of a specialist after taking photographs before the experiment and after 4 weeks. The results are represented in the below Table 9 (the Estimation grade: 0—No tightened; 5—very tightened).

TABLE 9

| Experimental materials | The estimation grade |
|---|---|
| Formulation Example 1 | 3.5 |
| Comparison Example 1 | 0.4 |

From the results of the above Table 9, since the Comparative Formulation Example 1 did not have the pore-tightening effect, but the Formulation Example 1 exhibited the pore tightening effect which can be identified by the naked-eye, it can be noted that the enzyme-treated saponin fraction derived from the root of *camellia sinensis* of the present invention has the excellent effect reducing the pore size.

Experimental Example 9

Effect for Inhibiting Sebaceum Secretion

<Effect for Inhibiting Sebaceum Over-Secretion by the Inhibition of 5α-Reductase Activity>

In order to identify the effect for inhibiting 5α-reductase activity, a ratio of [$^{14}$C]testosterone changed into [$^{14}$C] dihydrotestosterone (DHT) in HEK293-5αR2 cell was determined. HEK293 cell was transformed with p3×FLAG-CMV-5αR2 and $2.5×10^5$ cells/well were placed in 24-well plate and then incubated (Park et al., 2003, JDS. Vol. 31, pp. 191-98). The next day, new medium with the enzyme substrate and inhibitor was changed. 0.05 µCi [$^{14}$C]testosterone (Amersham Pharmacia biotech, UK) as the substrate of the medium was used.

In order to identify the degree of the inhibition of 5α-reductase activity, the saponin fraction derived from the root of *camellia sinensis* of Example 1 was put as an experimental material and incubated in 5% $CO_2$ incubator at 37° C. for 2 hours. At this time, the plate without the enzyme-treated saponin fraction derived from the root of *camellia sinensis* was used as a negative control, and that with finasteride was used as a positive control. Thereafter, the culture media was collected and steroid was extracted with 800 μl of ethylacetate and then, after separating the organic solvent layer of the top and drying it, the remaining residue was dissolved with 50 μl of ethylacetate and developed it by using ethylacetate-hexane (1:1) as a solvent on Silica plastic sheet kieselgel 60 F254.

The plastic sample was dried in the air, and Bath system was used to determine the amount of an isotope, in which the dried plastic sheet and X-ray film were put in Bath Cassette together to determine the amount of the isotope for testosterone and dihydrotestosterone remained on the film after 1 week and then a conversion and inhibition rates were calculated according to the mathematical formulae 3 and 4 as below, respectively, and the results are represented in Table 10 as below.

$$\text{Conversion rate (\%)} = \frac{\text{Radioactivity on } DHT \text{ region}}{\text{Total radioactivity}} \times 100 \quad \text{[Mathematic formula 3]}$$

$$\text{Inhibition rate (\%)} = \frac{\text{Conversion rate of the control} - \text{conversion rate of the Experimental material}}{\text{Conversion rate of the control}} \times 100 \quad \text{[Mathmatic formula 4]}$$

TABLE 10

| Experimental material | Conversion rate (%) | Inhibition rate (%) |
|---|---|---|
| Negative control | 48.0 | — |
| Positive control | 27.6 | 42.5 |
| Enzyme-treated saponin fraction derived from the root of *camellia sinensis* | 40.6 | 37.1 |

From the result of the Table 10, it could be identified that the enzyme-treated saponin fraction derived from the root of *camellia sinensis* of the present invention blocks the conversion of testosterone into dihydrotestosterone by effectively inhibiting 5α-reductase activity which plays a role in binding a receptor protein in the cytoplasm by conversing testosterone into dihydrotestosterone, entering into a nucleus to activate sebaceous gland cells and facilitate them to oversecrete the sebaceous. Therefore, it could be identified that the enzyme-treated saponin fraction derived from the root of *camellia sinensis* of the present invention effectively inhibits 5α-reductase activity to inhibit the oversecretion of sebaceous.

The Effect for Inhibiting the Secretion of Sebaceous Gland

In order to investigate the effect for inhibiting the sebaceous secretion for the Formulation Example 1 and the Comparative Formulation Example 1 as above, the following was estimated. Subjects, twenty of men and women who feel that sebaceous secretion is much were selected, divided into two groups, each one having 10 and then allowed them to apply the nourishing cream of the Formulation Example 1 or the Comparative Formulation Example 1 on the designated portion per each group every day for 4 weeks. The judgment for the effect for the sebaceous reduction was performed by determining the average sebaceous reduction rate (%) with Sebumeter SM 810 (C+K Electronic Co., Germany) after 2 weeks and 4 weeks, respectively, and the result is represented in Table 1 as below.

TABLE 11

| | Sebaceous reduction rate (%) | |
|---|---|---|
| Experimental material | After 2 weeks | After 4 weeks |
| Formulation Example 1 | 11 | 12 |
| Comparative Formulation Example 1 | 5 | 5 |

From the result of the above Table 11, it can be identified that the Formulation Example 1 comprising the enzyme-treated saponin fraction derived from the root of *camellia sinensis* of the present invention as the active ingredient can effectively inhibit the oversecreting sebaceous than the Comparative Formulation Example 1.

Experimental Example 10

Determination of the Effect for the Skin Moisturizing Ability Increasement

In order to determine the effect that the enzyme-treated saponin fraction derived from the root of *camellia sinensis* of the present invention affects the skin moisturizing ability increasement, the above Formulation Example 1 and the Comparative Formulation Example 1 were used, and estimated as follows.

Twenty of adult men and women aged 40~50 who were classified as having dryness skin were divided into two groups for each the Formulation Example 1 and the Comparative Formulation Example 1, each one having 10 and then allowed them to apply the nourishing cream twice every day for 4 weeks on face of them. The skin surface hydration was determined with the measuring instrument of the skin hydration, Corneometer CM825 (C+K Electronic Co., Germany) under the constant temperature and hyminity condition (24° C., the relative humidity 40%) before initiating the applying, at the time of 1 week, 2 weeks and 4 weeks after applying it, and after 2 weeks from the day stopping the applying (After total 6 weeks). The result is represented in Table 12 as below. The result of Table 12 is represented as the percent for the increased amount of the determination value after treating for a certain period, based on the value of the measuring instrument of the skin hydration just before initiating the Experiment.

TABLE 12

| | Percent of the moisture increasement (%) | | | |
|---|---|---|---|---|
| Experiment group | After 1 week | After 2 weeks | After 4 weeks | After 6 weeks |
| Formulation Example 1 | 27 | 27 | 27 | 24 |
| Comparative Formulation Example 1 | 30 | 32 | 32 | 15 |

Upon reviewing the result of the above Table 12, when applying the Comparative Formulation Example 1, although about 30% of the moisture increasement until 4 weeks performing the application was seen, the skin moisture amount was sharply decreased after stopping the application, but when applying the Formulation Example 1 comprising the enzyme-treated saponin fraction derived from the root of *camellia sinensis* of the present invention, most of 30% or more of the skin moisture increment rate could be identified after stopping the application. From this, it can be seen that the composition comprising the enzyme-treated saponin fraction derived from the root of *camellia sinensis* of the present invention has the excellent skin moisture ability effect.

Experimental Example 11

Determination of the Effect for Facilitating the Keratinocyte Differentiation

In order to investigate the effect of the enzyme-treated saponin fraction derived from the root of *camellia sinensis* for facilitating the differentiation of keratinocyte, the amount of the Cornified Envelop (CE) generated in the differentiation of the keratinocyte was determined by using the absorbance, as follows.

At first, human keratinocytes which ware isolated from the epidermis of the newborn baby and primary incubated were put in the flask for the cultivation to attach to the bottom and then were cultured until the cells grow to about 70~80% of the bottom dimension for 5 day after treating 5 ppm of concentration of the enzyme-treated saponin fraction derived from the root of *camellia sinensis* of the above Example 1 in the culture. At this time, the low calcium (0.03 mM) treated group and the high calcium (1.2 mM) treated group were designated as the negative control and the positive control, respectively. And then, the above cultured cells were harvested, washed with Phosphate buffered saline (PBS) and then added 1 ml of 10 mM Tris-Hydrochloric acid buffer (Tris-HCl, pH 7.4) comprising 2% Sodium Dodecyl Sulfate (SDS) and 20 mM Dithiothreitol (DTT), sonicated, boiled, and centrifuged, and then the sediment was suspended in 1 ml of PBS and the Absorbance at 340 nm was determined. Independently from this, some of the solution after the above sonication was taken, the content of the protein was determined, and was taken as a basis in estimating the degree of the differentiation of the cells. The result is represented in Table 13.

| Experimental material | Differentiation ability in keratinocyte (%) |
|---|---|
| Low calcium (0.03 mM) solution (Negative control) | 100 |
| High calcium (1.2 mM) solution (Positive control) | 210 |
| Enzyme-treated saponin fraction derived from the root of *camellia sinensis* | 138 |

As represented in the above Table 13, when treating the enzyme-treated saponin fraction derived from the root of *camellia sinensis*, it could be identified that the effect for facilitating the differentiation of the keratinocytes was excellent.

Experimental Example 12

Determination for the Effect Restoring a Skin Barrier Function

In order to determine the effect of the enzyme-treated saponin fraction derived from the root of *camellia sinensis* affecting the restoration of the skin barrier function damaged due to the skin damage, the following experiment was performed. Upper arms of ten of the adult men and women were damaged on their skin barrier by using Tape Stripping method and the degree of the restoration of Transepidermal Water Loss (TEWL) was determined with Vapometer (Delfin, Finland) once a day for 7 days while applying two groups of the Formulation 2 and Comparative Formulation Example 2 made of the composition of the below Table 14, respectively and compared with each other. In this case the Comparative Formulation 2 is a vehicle as the negative control. The experimental result is represented in Table 15 as below. The result of Table 15 was compared based on 100% being the difference between before the barrier damage and before the treatment after the barrier damage.

TABLE 14

| Combination components | Formulation 2 | Comparative Formulation 2 |
|---|---|---|
| Purified water | 69 | 69 |
| Propylene glycol | 30 | 30 |
| Enzyme-treated saponin fraction derived from the root of *camellia sinensis* (Example 1) | 1 | — |

TABLE 15

| Experimental group | Before treatment | TEWL Change (%) | | | | | |
|---|---|---|---|---|---|---|---|
| | | 1 day | 2 day | 3 day | 4 day | 5 day | 6 day |
| Formulation Example 2 | 100 | 125.3 | 105.2 | 84.2 | 60.2 | 48.1 | 32.1 |
| Comparative Formulation Example 2 | 100 | 121.4 | 112.7 | 98.3 | 70.5 | 62.3 | 43.5 |

As can be seen from the above Table 15, when treating the composition comprising the enzyme-treated saponin fraction derived from the root of *camellia sinensis*, it could be identified that the transepidermal water loss was returned to a normal rapidly and the barrier damage was restored.

Formulation Example 3 and Comparative Examples 3-4

Formulation Example 3 and Comparative Examples 3~4 were prepared according to the components and contents (wt %) as represented in Table 16 as below. More specifically, the Formulation Example 3 was one combined with the enzyme-treated saponin fraction derived from the root of *camellia sinensis*, the Comparative Formulation Example 3 was one without the active ingredient improving an acne skin, and the Comparative Formulation Example 4 was one containing erythromycin widely used as an acne treating agent, as a standard material of a standard for the antibacterial activity.

The preparation method of Formulation Example 3 and the Comparative Formulation Examples 3~4 are as follows. Components on A phase of the below Table 16 were completely dissolved and components on B phase were completely dissolved in a separate dissolver and then, B phase was added to A phase and mixed them to be solubilized. Components on C phase were added according to the combination ratio as described in Table 16 and mix-homogenized and then filtered it to make the compositions of the present invention.

TABLE 16

| | Classification | Formulation Example 3 | Comparative Formulation Example 3 | Comparative Formulation Example 4 |
|---|---|---|---|---|
| A | Deionized Water | to 100 | to 100 | to 100 |
| | EDTA-2Na | 0.02 | 0.02 | 0.02 |
| | Glycerine | 5.0 | 5.0 | 5.0 |
| B | Ethanol | 2.0 | 2.0 | 2.0 |
| | PEG-60 hydrogenated castor oil | 0.4 | 0.4 | 0.4 |
| | Perfume | 0.04 | 0.04 | 0.04 |
| C | Enzyme-treated saponin fraction derived from the root of camellia sinensis (Example 1) | 5.0 | — | — |
| | Erythromycin | — | — | 5.0 |

Experimental Example 13

Experiment for the Anti-Bacterial Activity for the Acne Germs

The anti-bacterial activity for *Propionibacterium acnes* <ATCC 6919: medium-BHI broth> which is a causative strain for acne was tested with each cosmetic composition of Formulation 3 and Comparative Formulation Examples 3~4.

The test method for the anti-bacterial activity was as follows.

(1) Preparation of the Test Strain Liquid

*Propionibacterium acnes* used a culture which anaerobic cultured by inoculating on BHI broth.

(2) Preparation of the Diluted Solution 0.15 ml of the above test strain was added to 15 ml of BHI Broth (pH 6.8) or LB broth (pH 4.5) and mixed thoroughly and then used as the diluted solution.

(3) Preparation of the Sample

The stock solution of the cosmetic composition prepared from the Formulation Example 3 and the Comparative Formulation Examples 3~4 was used intactly as a sample.

(4) Test for the Anti-Bacteria Activity

1) Samples were put on the first line of 96-well plate to fit the starting concentration and the diluted solution was put to the total 200 μl, respectively.

2) Double dilution was performed in the manner that mixtures on the first line were mixed thoroughly and 100 μl was taken and put in the second line and mixed, and then 100 μl was taken and put the third line, and so on.

3) After the static culturing at the temperature of 32° C. for 24 hours and 48 hours, it was determined whether the strain was proliferated or not based on the suspended degree and then the minimum concentration without the proliferation of strains was determined as Minimum Inhibitory Concentration (MIC). If the mixture was opaque and thus it was difficult to determine as to whether strains were proliferated or not, it was identified through the microscopy.

The test result of the anti-bacterial activity for acne germs was represented in Table 17 as below. MIC was recorded after converting it to the concentration of the active ingredients contained in the formulation.

TABLE 17

| Items | pH | MIC of *Propionibacterium acnes* (ppm) |
|---|---|---|
| Formulation Example 3 | 5.7 | 15.4 |
| Comparative Formulation Example 3 | 5.7 | maximum concentration (no anti-bacterial activity) |
| Comparative Formulation Example 4 | 5.7 | >100 |

Lower the ppm concentration in MIC, it could be said as being more effective material in the anti-bacterial activity for acne germs. Since the ppm concentration of the formulation 3 was greatly lower than that of the Comparative Formulation Example 4 using the known acne treating agent, erythromycin, it could be identified that the composition comprising the enzyme-treated saponin fraction derived from the root of *camellia sinensis* has much more excellent anti-bacterial activity for the test strain.

Experimental Example 14

Inhibitory Test for Lipogenesis

3T3-L1 cells of fibroblast cell line of a rat were attached to 6-well culture plate with Dulbecos modified eagles medium (DMEM) (GIBCO BRL, Life Technologes Co.) containing 10% fetal bovine serum (FBS) at $1\times10^5$ cells/well. After 2 days, new DMEM (comprising 10% FBS) was exchanged and cultured for 2 days. Then, the cultured cells were induced the differentiation with DMEM (comprising 10% FBS) comprising fig/ml insulin, 0.25 μM dexamethasone and 0.5 mM IBMX and treated with 50 μM of the enzyme-treated saponin fraction derived from the root of *camellia sinensis* of the above Example 1 and caffeine, and then after 2 days, exchanged with DMEM with insulin and cultured for 5 days. After 5 days, the culture was exchanged with the normal medium (DMEM, comprising 10% FBS) and incubated with observing that the above cells ore changed into fat cells morphologically.

In order to estimate the efficacy of the enzyme-treated saponin fraction derived from the root of *camellia sinensis* for the efficacy inhibiting the fat accumulation in fat cells, sudan III staining (S4136, Sigma-Aldrich) by using 3T3-L1 fat cells which had completed the differentiation in the above was performed. After fixating the fat cells in a phosphate buffer with 4% paraformaldehyde (pH 7.2) at the room temperature, it was washed with phosphate buffered saline (PBS) and then took photographs after staining with Sudan III and compared with the naked eye. The control was one using only the medium without adding the test material or the comparative material, and another comparative group is one treated with 50 μM caffeine. The degree inhibiting the fat accumulation was graded by dividing the dyed degree into +++, ++, +, and –. The results are represented in Table 18 as below.

TABLE 18

| Sample | Inhibition rate (%) |
|---|---|
| Control | + + + |
| Comparative group | + |
| Enzyme-treated saponin fraction derived from the root of camellia sinensis | + |

As represented in the above Table 18, it can be seen that the enzyme-treated saponin fraction derived from the root of *camellia sinensis* used in the present invention has the effect inhibiting lipid synthesis. Therefore, sebaceum can be reduced by inhibiting the lipid synthesis to inhibit the occurrence of acne.

Experimental Example 15

Test for the Improvement of Acne, the Reduction of Sebaceum Secretion and the Presence or Absence of the Stimulation Thirty humans possessing acne were divided into three groups with each one having 10 and then allowed the subjects corresponding to each group to apply the costimatic composition prepared from the above Formulation Example 3 and the Comparative Formulation Examples 3~4 for 1 month. The criteria for improving acne were assigned 1 to 5, and made mark as score 1: 'No', score 3: 'Normal', and score 5: 'so yes'. The experimental result was recorded as the average score of ten in Table 19.

The time for disappearing acne was based on the number of days at which the disappearance was read, the recurrence of acne was recorded as the presence or absence of it, based on the result after 1 month. The reduction of sebaceum secretion was assigned as score 1 to score 5, and was recorded as score 1: 'No', score 3: 'Normal' and score 5 'So yes'. The test result was recorded as the average score of ten in the below Table 19. The presence or absence of the skin stimulation was considered as (numbers of persons showing the stimulation response)/(total number of persons tested).

TABLE 19

|   | Improvement of inflammative acne | The time for disappearing comedo acne | Recurrence of acne | Reduction of sebaceum secretion | Present or absence of the stimulation |
|---|---|---|---|---|---|
| Formulation Example 3 | 3.5 | 4 days | absence | 3.8 | 1/10 |
| Comparative Formulation Example 3 | 2.1 | 13 days | presence | 2.0 | 0/10 |
| Comparative Formulation Example 4 | 4.2 | 2 days | absence | 4.1 | 9/10 |

As represented in the above Table 19, it could be seen that the Formulation Example 3 was more effective than the Comparative Formulation Example 3 in protecting the recurrence of the acne, and generally has the superior effect in the improvement of the acne. Meanwhile, in the case of the Comparative Formulation Example 4 comprising anti-bacterial activity standard material, although it exhibits the acne improvement effect, since the stimulation is strong in using it, it was apprehended the skin stimulation in using it for a long-time, but it is appeared that the composition of the present invention has the weak or no stimulation over the Comparative Formulation Example 4.

The Experimental Example 16

The Effect for Improving Inflammation

The anti-inflammation effect was estimated as the effect inhibiting the generation of prostaglandin. The effect was determined on the macrophase by using the enzyme-treated saponin fraction derived from the root of *camellia sinensis*.

At first, cyclooxygenase (COX) activity was irreversibly inhibited by adding aspirin to the macrophage obtained from celiac of a mouse to be 500 μM of the final concentration. Then, 100 μl of the above suspension was put in each well of 96-well cell cultivation tube and cultured in the incubator under the condition of 5% $CO_2$ and 37° C. for 2 hours to attach the macrophase to the surface of the container. Thereafter, the attached macrophage was washed with PBS three times and was used in the test for the inflammation improvement effect. RPMI medium comprising 1% (w/v) of lypopolysaccaride (LPS) was added to the cultured macrophase of $4\times10^4$ cells/ml followed by culturing the macrophase for 12 hours. Then the generation of prostaglandin was caused, and the macrophase was treated with 100 μl of the enzyme-treated saponin fraction derived from the root of *camellia sinensis* of the above Example 1 and prostaglandin liberated was quantified by using Enzyme-Linked Immuno-Sorbent Assay (ELISA).

At this time, the activity inhibiting prostagladin generation of saponin fraction derived from the root of *camellia sinensis* was set as 100% for the difference of the prostaglandin generated from the group treated with LPS and the group not-treated with LPS, respectively, and compared it with the control through the percent of the prostaglandin reduced by treating the sample with LPS, and then the result (the effect for inhibiting the prostaglandin generation) was represented in Table 20 as below.

TABLE 20

| Blank | 100% |
|---|---|
| Control (group treated with aspirin) | 25.0% |
| Enzyme-treated saponin fraction derived from the root of *camellia sinensis* | 39.% |

As can be seen in the above Table 20, as a result of the test, it can be seen that the effect inhibiting the prostaglandin generation effect in the group treated with the enzyme-treated saponin fraction derived from the root of *camellia sinensis* was very high like the control treated with aspirin.

From the above result, it can be seen that the enzyme-treated saponin fraction derived from the root of *camellia sinensis* of the present invention provides the superior inflammation improvement effect.

In addition, it can be seen that the saponin fraction derived from the root of *camellia sinensis* can prevent and improve the skin trouble by inhibiting the expression of prostaglandin which is the skin inflammation factor.

Experimental Example 17

A Skin Whitening Effect
<Tyrosinase Hinderance Effect>

Tyrosinase enzyme is that extracted from Mushroom and used the product of SIGMA Company. At first, tyrosine being the substrate was dissolved in the distilled water to make 0.3 mg/ml of solution and 1.0 ml of each solution was put in the tube, and then, 1.0 ml of potassium-phosphate buffer solution (0.1 mol concentration, pH 6.8) and 0.7 ml of the distilled water were added.

Each sample liquid, 0.2 ml, which was prepared by mixing the enzyme-treated saponin fraction derived from the root of *camellia sinensis* of the above Example 1 of the present invention in ethanol solution in the proper concentration was put in the reaction liquid and then was reacted in 37° C. incubator for 10 minutes. At this time, the control was prepared by adding only 0.2 ml of solution, instead of each of sample liquid, ascorbic acid was used as the positive control. 0.1 ml of 2500 units/ml tyrosinase solution was added to the reaction liquid and reacted in 37° C. incubator for 10 minutes. The tube with the reaction liquid was put in the ice water to stop the reaction by quenching and the absorbance at the wavelength of 475 nm was determined with the photoelectric spectrophotometer, and then the result was represented in the below Table 21. Each of tyrosinase hinderance effect was calculated by the below mathematical formula 5.

$$\text{Tyrosinase hinderance rate (\%)} = 100 - \left( \frac{\text{Reaction absorbance of the test material}}{\text{Reaction Absorbance of the control}} \times 100 \right) \quad \text{[Mathematical formula 5]}$$

TABLE 21

| Test material | Tyrosnase hinderance rate (%) |
|---|---|
| Control (no addition) | 0 |
| Ascorbic acid | 52 |
| Enzyme-treated saponin fraction derived from the root of camellia sinensis | 58.1 |

From the result of the above Table 21, it was exhibited that the enzyme-treated saponin fraction derived from the root of camellia sinensis of the present invention has the tyrosinase inhibition rate equal or more when comparing it with ascorbic acid as the known tyrosinase inhibitor, and thus, it could be seen that the whitening effect was very excellent.

The Effect for Inhibiting Melanin Generation by Using B16/F10 Melanoma Cell

The sample comprising 0.001 wt % of the saponin fraction derived from the root of camellia sinensis of the above Example 1 and kojic acid, respectively, as the test material, was added to the culture of B16/F10 melanoma cell (Korean cell strain bank) at the constant concentration and cultured for 3 days, washed with PBS, dissolved with 1N NaOH and the absorbance was determined at 405 nm. At this time, the cell added no test material was considered as the control and the degree for hindering the melanin generation of each test material was determined by comparing the contents of melanin in the control. The inhibition rate of melanin generation was calculated according to mathematical formula 6 as below and its result was represented in Table 22.

$$\text{Inhibition rate of melanin generation (\%)} = 100 - \left( \frac{\text{Absorbance of the test material}}{\text{Absorbance of the control}} \times 100 \right) \quad \text{[Mathematical formula 6]}$$

TABLE 22

| Test material | Inhibition rate of melanin generation (%) |
|---|---|
| Conrol (no addition) | 0 |
| Kojic acid | 53 |
| Enzyme-treated saponin fraction derived from the root of camellia sinensis | 62.1 |

From the result of the above table 22, it was exhibited that the enzyme-treated saponin fraction derived from the root of camellia sinensis of the present invention has the inhibition rate of melanin generation to the extent which is equal to or more than that of Kojic acid being the known melanin generation inhibitor upon comparing with the Kojic acid, and thus, it could be seen that the whitening effect of the present invention was very excellent.

Experimental Example 18

The Effect for Improving Atopic Syndrome
Estimation of Itching Mitigation

Keratinocytes (Cell line name: HaCaT, obtained from ATCC) were seeded to be 4×10⁴ cells/well in 96-well plate one day before the test day and were cultured at 37° C., 5% $CO_2$ incubator for 24 hours. After 24 hours, 96-well plate was washed with Hanks' Balanced Salt solution (HBSS) buffer twice and then the reaction buffer (2 μM Fluo-4-AM, 20% pluronic acid, 2.5 mM probenecid) was put into the cells. After reacting the cells at 37° C., 5% $CO_2$ incubator for 30 minutes, and at room temperature for 30 minutes, they were washed with HBSS buffer twice and treated with 0.1% of the enzyme-treated saponin fraction derived from the root of camellia sinensis of the above Example 1. At this time, the medium without treating with the test material was used as the control.

After reacting for 10 minutes, the cells were treated with 2 U/ml trypsin or 5 μM PAR-2 active peptide (SLIGKV) and the $Ca^{2+}$ concentration change in the cells was determined for 80 seconds. The determination of $Ca^{2+}$ concentration change in the cells was performed by using FlexStation 3 (Molecular Device, USA). After treating it with 2 U/ml trypsin or 5 μM PAR-2 active peptide (SLIGKV), the difference between the maximum value and the minimum value of values obtained by determining the flex for 80 seconds was calculated, and then compared the value with the difference between the minimum value and maximum value when treating 2 U/ml trypsin or 5 μM PAR-2 active peptide (SLIGKV) and the inhibition rate (%) for endocytosis of calcium ions was represented in Table 23 as below.

TABLE 23

| | Inhibition rate for endocytosis of calcium ions (%) | |
|---|---|---|
| Classification | Trypsin (2 U/ml) | PAR-2 active peptide (5 μM) |
| Untreated control | 10 | 15 |
| Enzyme-treated saponin fraction derived from the root of camellia sinensis | 21 | 25 |

As can be seen from the above Table 23, when the enzyme-treated saponin fraction derived from the root of

*camellia sinensis* was treated, it can be identified that endocytosis of calcium ions by trypsin or PAR-2 active peptide (SLIGKV) was reduced.

Therefore, the skin composition for external use of the present invention can provide the superior anti-itching effect by effectively inhibiting PAR-2 activity.

Estimation of the Anti-Inflammatory Efficacy

Normal human skin keratinocytes (NHEK, Lonza) were seeded to be $5 \times 10^4$ cells/well in 96-well plate one day before the test day and were cultured at 37° C., 5% $CO_2$ incubator for 24 hours. After 24 hours, the cells were washed with PBS twice and serum free keratinocyte basement media (KBM) was exchanged. After treating each well with 30 ppm of the saponin fraction derived from the root of *camellia sinensis* of the above Example 1 and reacting it for 30 minutes, PGSA (50 µg/ml)+LPS (1 µg/ml) were treated. In addition, for the comparison, the well untreated the saponin fraction derived from the root of *camellia sinensis* was treated with PGSA (10 µg/ml), PGSA (50 µg/ml) or PGSA (50 µg/ml)+LPS (1 µg/ml), respectively. In addition, the medium not treated with the test material was used as the control. In this case, peptidoglycan from *S. aureus* (PGSA) is the major constitutive component of cell wall of gram positive (+) strains as peptidoglycan extracted from *Staphylococcus* and the components of the cell membrane of bacteria have been known to cause the inflammation, in particular, in the case of *Staphylococcus*, it has been reported that the secondary infection by such strains is caused in 90% of atopic patients. Lypopolysaccaride (LPS) is the major constitutive component of cell membrane of bacteria strains and has been known as the major cause inducing the inflammation.

After culturing it at 37° C., 5% $CO_2$ incubator for 24 hours, the culture was taken and proceeded ELISA for Interleukin-8 (IL-8), and its result was represented in Table 24 as below. ELISA used the experimental method of the manufacturer (BD science).

TABLE 24

| Classification | IL-8 secretion (pg/ml) |
| --- | --- |
| Untreated control | 935.12 |
| PGSA (10 µg/ml) | 4812.60 |
| PGSA (50 µg/ml) | 5895.08 |
| PGSA (50 µg/ml) + LPS (1 µg/ml) | 6814.91 |
| Enzyme-treated saponin fraction derived from the root of *camellia sinensis* | 5955.4 |

From the above Table 24, it could be identified that the enzyme-treated saponin fraction derived from the root of *camellia sinensis* reduced and inhibited the IL-8 secretion increased by PGSA and LPS.

Therefore, the composition for applying the external of the skin external of the present application can provide the superior anti-inflammation effect by reducing IL-8 secretion increased by PGSA and LPS.

The invention claimed is:

1. A topical composition for treating acne in a human in need thereof consisting essentially of a therapeutically effective amount of green tea root extracted with an alcohol and then treated with an enzyme at pH 3.5-5.0 at 25° C.-60° C., wherein said enzyme is selected from the group consisting of glucosidase, xylosidase, xylanase, galactosidase, naringinase, pectinase, cellulose, hemicellulase and arabinose.

* * * * *